US011510657B2

(12) United States Patent
Omero et al.

(10) Patent No.: US 11,510,657 B2
(45) Date of Patent: Nov. 29, 2022

(54) ULTRASOUND DIAGNOSTIC SYSTEM WITH MULTIMEDIA INFORMATION DISTRIBUTION SYSTEM

(71) Applicant: Esaote, S.P.A., Genoa (IT)

(72) Inventors: Massimiliano Omero, Genoa (IT); Luca Muraca, Genoa (IT)

(73) Assignee: Esaote, S.p.A., Genoa (IT)

( * ) Notice: Subject to any disclaimer, the term of this patent is extended or adjusted under 35 U.S.C. 154(b) by 207 days.

(21) Appl. No.: 16/401,519

(22) Filed: May 2, 2019

(65) Prior Publication Data

US 2019/0350563 A1 Nov. 21, 2019

(30) Foreign Application Priority Data

May 21, 2018 (EP) .................................... 18173410

(51) Int. Cl.
| | |
|---|---|
| *A61B 8/00* | (2006.01) |
| *H04N 21/2187* | (2011.01) |
| *H04N 21/234* | (2011.01) |
| *H04N 21/2343* | (2011.01) |
| *H04N 21/238* | (2011.01) |
| *H04N 21/24* | (2011.01) |
| *H04N 21/835* | (2011.01) |

(52) U.S. Cl.
CPC .............. *A61B 8/565* (2013.01); *A61B 8/469* (2013.01); *H04N 21/2187* (2013.01); *H04N 21/2343* (2013.01); *H04N 21/23424* (2013.01); *H04N 21/23805* (2013.01); *H04N 21/24* (2013.01); *H04N 21/835* (2013.01)

(58) Field of Classification Search
CPC .... A61B 8/565; A61B 8/469; H04N 21/2187; H04N 21/23424; H04N 21/2343; H04N 21/23805; H04N 21/24; H04N 21/835
See application file for complete search history.

(56) References Cited

U.S. PATENT DOCUMENTS 9,699,518 B2 * 7/2017 Ohbitsu ............... H04N 19/164
2002/0172498 A1 11/2002 Esenyan et al.
(Continued)

OTHER PUBLICATIONS

European Search Report for Application No. 18173410.4 dated Jul. 12, 2018.
(Continued)

*Primary Examiner* — Oschta I Montoya
(74) *Attorney, Agent, or Firm* — Woodard, Emhardt, Henry, Reeves, and Wagner, LLP

(57) ABSTRACT

An ultrasound system with a multimedia information distribution system comprising:
  a video processor generating a sequence of video frames of at least the ultrasound diagnostic images of a sequence of ultrasound diagnostic images;
  a media editor for combining the ultrasound video frames with further audio/video data to generate multimedia data;
  a multimedia encoder encoding the multimedia data in the form of a multimedia file;
  a media streaming module receiving the said multimedia file and generating a real-time stream of the sequence of multimedia data encoded in the said multimedia file;
  a web server allowing access to the real-time stream of the multimedia data upon request by a remote client to access the said multimedia file.

A corresponding computer implemented method is also disclosed.

16 Claims, 9 Drawing Sheets

(56) References Cited

U.S. PATENT DOCUMENTS

| | | | |
|---|---|---|---|
| 2005/0251040 A1 | 11/2005 | Relkuntwar et al. | |
| 2007/0094052 A1* | 4/2007 | Blas | G16H 15/00 705/3 |
| 2009/0028453 A1* | 1/2009 | Collomosse | H04N 1/32251 382/243 |
| 2013/0208955 A1* | 8/2013 | Zhao | G06F 19/321 382/128 |
| 2017/0249424 A1* | 8/2017 | Augusto Di Grandi Nery | G16H 10/60 |
| 2020/0162794 A1* | 5/2020 | Nishino | H04N 21/2668 |

OTHER PUBLICATIONS

Product Overview. Discover the Fascinating World of PENTAX Medical Endoscopy. Dec. 9, 2017. Retrieved from Internet on Nov. 7, 2018.

Sonostream LIVE!—What is Sonostream?, Aug. 26, 2017, Retrieved from Internet on Nov. 9, 2018.

Introduction to Streaming Media. In: The Technology of Video and Audio Streaming, Oct. 4, 2004. Taylor & Francis Group. pp. 133-153.

Stream Serving. In: The Technology of Video and Audio Streaming, Oct. 4, 2004, Taylor & Francis Group. pp. 209-232.

Video Encoding. In: The Technology of Video and Ausio Streaming, Oct. 4, 2004. Taylor & Francis Group. pp. 154-178.

What is streaming? In: The Technology of Video and Audio Streaming, Oct. 4, 2004, Taylor & Francis Group. pp. 7-8.

Advantages of Multimedia Streaming. Web Page May 30, 2018. Extracted on May 1, 2019.

Endoskopischer Ultraschall, Pentax Medical (Germany). Retrieved from Internet May 1, 2019.

\* cited by examiner

ULTRASOUND DIAGNOSTIC SYSTEM WITH MULTIMEDIA INFORMATION DISTRIBUTION SYSTEM

BACKGROUND OF THE INVENTION

The present disclosure relates to an ultrasound diagnostic system with multimedia information distribution system.

Ultrasound diagnostic systems are known since the 1990's. The usual ultrasound systems comprise specialized workstations, ultrasound user interfaces for facilitating the diagnosis. Storage devices allow to retrieve the diagnostic images acquired and to study the images for diagnostic purposes off-line, at a later time than acquisition or to carry out follow up studies. Ultrasound systems are also provided with network connection units allowing to integrate the ultrasound systems in a network and to transmit or receive diagnostic information to and from remote servers or workstations.

Ultrasound systems are known which have a remote access port allowing to carry out remote upgrade and maintenance operation of the system.

Quality of the diagnostic data acquired with the ultrasound system depends inter alia also from the skill of the operator in manipulating the probe and in selecting the proper settings or imaging mode of the system.

Furthermore, the diagnostic information has to be read from the acquired data so that also a certain level of skill is relevant in reading the images or other data acquired.

Since there is a trend to reduce or limit increase of healthcare costs, one of the ways to achieve this goal is to reduce the intervention of persons having a high specialist education in carrying out operations that can be carried out by specialized person having a lower educational level. This trend requests more efforts in training of specialist skills in acquiring images for the ultrasound system operators and in reading and evaluating the acquired data for the doctors in order to identify with more certainty clinical and health conditions or pathologies of the patients from the acquired data.

In order to maintain low the costs of the specific education the transmitted information should be made available to a very large number of persons. Current systems allow this kind of wide spread distribution in an off-line mode in which recorded information relating to the acquired data by the ultrasound system and to information about the techniques of manipulating the probe and of setting the ultrasound system is distributed after having been recorded. This way is indirect and does not allow an immediate feedback of the audience with the acquisition process.

Furthermore, there are also cases in which there is the need to distribute or broadcast in real time the acquired information optionally together with the indications given by the operator relating to the information reproduced in the images without needing specialized hardware or software for reading the stored image data in the typical format used by the ultrasound system. Using the streaming feature provided by the present invention this image data can be transmitted to every kind of client apparatus through wired or wireless connection.

One example relates to relatives not being present at the site where the imaging session is carried out and who wants to have the possibility to see the images and receive the possible comments in real time even they are staying in a remote site.

SUMMARY OF THE INVENTION

An object of the present disclosure consists in providing an ultrasound system with a multimedia information distribution system capable of allowing a universal and real-time access to the acquired information particularly to the acquired image data.

A further object is to provide an ultrasound system which allows to integrate the acquired image information with other information and to select the blend of the information to be distributed.

A further object is to provide an ultrasound system which allows to select the information content depending on the requests of the audience or of other criteria identifying specific features of the audience.

Still a further object of the present disclosure is to provide an ultrasound system requesting conventional hardware and software for accessing the information.

A further object consists also in providing the ultrasound system with capabilities of automatically optimizing the data stream in relation to the remote user hardware and software in order to have the best reproduction of the multimedia content.

According to a first embodiment an ultrasound system with a multimedia information distribution system is provided comprising:

a video processor generating a sequence of video frames of at least the ultrasound diagnostic images of a sequence of ultrasound diagnostic images;

a video encoder encoding the sequence of ultrasound images in the form of a video file;

a media streaming module receiving the said video file and generating a real-time stream of the sequence of video frames encoded in the said video file;

a web server allowing access to the real-time stream of the video frames upon request by a remote client to access the said video file.

According to an embodiment in combination with the above ultrasound system a client is provided comprising:

A processing unit executing a web browser and/or a media file reader executed by the said processor or by a dedicated graphic processor;

Input devices for generating a request of access;

Two-way communication units for sending the request of access to a web server and for connecting to the web server and receiving the video.

According to an embodiment, the ultrasound system comprises a sound processor for generating audio data and a media editor for combining audio digital data to the video frames generating multimedia data, the said multimedia data being encoded as a multimedia file and being fed to the media streaming module.

According to an embodiment the ultrasound system comprises in addition a text processor for transforming digital alphanumeric information in video frames, the said video frames being fed to the said media editor which is configured to combine the said alphanumeric information (textual information) with the video frames representing the ultrasound images and the acoustic data and generating combined multimedia data fed to the multimedia encoder for generating multimedia files.

Still according to an embodiment, the ultrasound system comprises a GUI image processor for transforming the GUI image in GUI video frames, the said GUI video frames being fed to the said media editor which is configured to combine the said GUI video frames with the video frames representing the ultrasound images and/or the video frames representing the textual information and/or the acoustic data and generating combined multimedia data fed to the multimedia encoder for generating multimedia files.

A further embodiment the ultrasound system is provided with at least a camera oriented to catch a field of view encompassing at least the ultrasound probe, the hand of the operator and the area of use of an object under examination or the entire ultrasound system, the object to be examined and the operator, the video frames captured by the said camera being fed to the said media editor which is configured to combine the video frames captured by the camera with the said GUI video frames and/or with the video frames representing the ultrasound images and/or with the video frames representing the textual information and/or with the acoustic data and generating combined multimedia data fed to the multimedia encoder for generating multimedia files.

In an embodiment the ultrasound system is provided in combination with at least a microphone for capturing the environmental sounds and especially the voice of at least one operator of the ultrasound system the said audio data captured by the microphone being fed to the said media editor which is configured to combine the said audio data with the said video frames of the camera and/or with the said GUI video frames and/or with the video frames representing the ultrasound images and/or with the video frames representing the textual information and/or with the acoustic data and generating combined multimedia data fed to the multimedia encoder for generating multimedia files.

According to an embodiment which can be provided in any combination or sub combination with the features of the above disclosed embodiments, the ultrasound system is provided with an access controller unit configured to receive access rights certificates and validate the said access rights certificate by comparing in a comparator unit the said access rights certificates with a database of registered access rights certificates stored in a memory and allowing access to the web browser of a remote client unit to the multimedia streaming module.

According to a variant embodiment, the access rights certificates are related with selection parameters of the information being available for the owner of the said certificate, the said selection parameter being registered in the database of access rights certificates and the access right controller sending the said selection parameter to a data content controller driving a data selector unit which operates the media data editor to combine only multimedia data related to information available for the corresponding access right certificate.

According to a further improvement, a graphic banners generator is provided generating banners for covering or blending out display area in which non available information for a specific access right certificate are displayed, the said graphic banner generator feeding the banner image to the media data editor for combining the image of the said banner with one or more of the said video frames of the camera and/or with the said GUI video frames and/or with the video frames representing the ultrasound images and/or with the video frames representing the textual information.

According to a further embodiment which can be provided alone or in combination with one or more of the above embodiments, a controller measuring the frame rate of the displayed frames on the display of the client is provided, the said controller measuring the frame rate of the displayed frames and drive a video frame discarding unit from the multimedia data stream configured to eliminate video frames from the said multimedia data stream and optionally the associated acoustic data when the frame rate of the displayed frames falls below a certain threshold, an input interface being also provided for setting the said threshold.

According to still a further embodiment in order to limit the band occupied by the multimedia stream of data the media data editor comprises a comparator unit comparing each following video and/or acoustic frame with the preceding one and discards from the multimedia file to be generated the video frames being identical with the preceding ones maintaining only the video frames which are different from the preceding ones.

Thanks to this improvement frames which do not add any information are automatically discarded.

According to still a further improvement in order to maintain the frame rate the preceding video frame corresponding to an identical following videoframe is frozen as long as a new following frame is present which is different from the said frozen preceding one.

According to an embodiment the above disclosed units may be all or in part configured as a hardware or the said unit may consist all or in part in software programs containing the instruction which configure a generic processor to carry out the steps of the corresponding unit.

The invention relates also to a method for distributing visual acoustic and textual information generated by an ultrasound system to remote clients, the said method comprising the steps of:

Generating video, audio and textual data by an ultrasound scanner;

Processing in real time the video, acoustic and textual data for generating a multimedia file combining at least one or more of the said video, acoustic and textual data;

Providing a web server to allow access to the said multimedia file in real time with the said generation step.

The said method further comprises the steps of providing at least a client connecting the said web server by executing a web browser.

According to a further embodiment, the said method comprises the steps of:

Providing each client with access certificates; Associating each certificate to a selection parameter determining the kind of information being available for a corresponding certificate;

Covering or discarding from the displayed video frames the information which is not available for the corresponding ace right certificate.

According to still a further embodiment of the present method there is provided transmitting in the stream of video frames only the video frames having a difference in content from the previous one by Comparing each video frame with the preceding one;

Discarding the identical video frame and freezing the preceding one on the screen;

Transmitting for display the following video frame which has differences from the frozen previous one and displaying the said following video frame According to still a further embodiment of the above method which can be provided in any combination with the preceding embodiments, the steps are provided of monitoring the frame rate of the displayed video frames by the client;

Comparing the frame rate with a threshold;

Suppressing or discarding from the stream some video frames if the frame rate of the displayed frames is lower than the said threshold.

DESCRIPTION OF THE EMBODIMENTS

Figure 1:
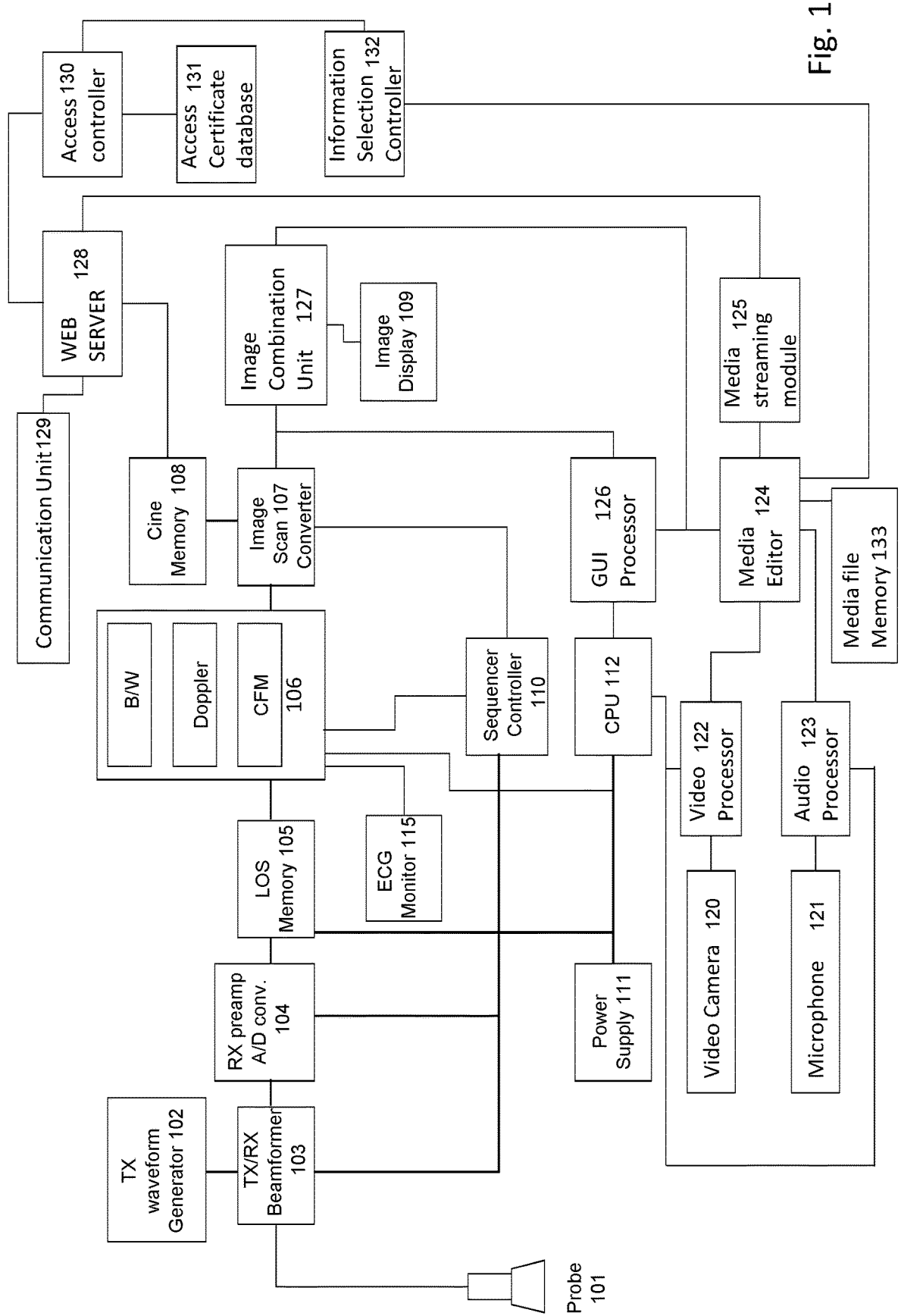
FIG. 1 is a high level diagram of an embodiment of an ultrasound system according to the present invention.

FIG. 1 illustrates a high-level block diagram of an ultrasound system according to an embodiment. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 1 includes one or more ultrasound probes 101. The probe 101 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The beamformer 103 supplies transmit signals to the probe 101 and performs beamforming of "echo" signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, color Doppler imaging, pulse-inversion transmit techniques, contrast-based imaging, M-mode imaging and the like. The beamformer 103 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 104. The RF beamformed signals are converted to I,Q data pairs.

The I, Q data pairs are saved as image pixels in the line of sight (LOS) memory. For example, the LOS memory may include LOS memory portions associated with each line of sight through the ROI. The I,Q data pairs, defining the image pixels for corresponding individual ROI locations along a corresponding LOS, are saved in the corresponding LOS memory portion. A collection of image pixels (e.g., I,Q data pairs) are collected over time and saved in the LOS memory 105. The image pixels correspond to tissue and other anatomy within the ROI.

In embodiments, a dedicated sequencer/timing controller 110 may be programmed to manage acquisition timing which can be generalized as a sequence of firings. The sequence controller 110 manages operation of the TX/RX beamformer 103 and the A/D converter 104.

One or more processors 106 perform various processing operations as described herein. The CPU 112 may perform control operations of various units such as the processors 106, the GUI-image processor 162, the video processor 122 and the sound or audio processor 123.

Among other things, the processor 106 and/or CPU 112 analyse the image pixels to determine differences between each following image from a preceding one of a time sequence of images and to control the video processors and/or the media editor or the streaming module 125 in order to discard from the data stream images which are identical or almost identical to the previous one by maintaining on screen the previous image.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown. Optionally, the system of FIG. 1 may include an ECG monitor not shown that couples an ECG sensor to the patient and records an ECG signal indicative of the patient's heart rate. The processor 106 and/or sequence controller 110 synchronize the image acquisition steps with the ECG signal.

The blocks/modules illustrated in FIG. 1 can be implemented with dedicated hardware (DPSs, FPGAs, memories) and/or in software with one or more processors.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuits, modules, processors, memory components, and the like. The power front-end may be an A.C. power source and/or a battery power source (e.g., in connection with portable operation).

According to a further feature an image combination unit 127 may be present in which the B-mode image data of at least of a region of interest and the corresponding graphic representation of the GUI and further textual information associated to the image acquisition such as data of the patient, indication of the diagnosis, setting of the scanner is combined for the superimposed display of the B-mode image and of the said data.

The acquired images as well as the GUI images and the textual data are combined in the Image combination unit and the combined images are displayed on the image display of the ultrasound system.

The said acquired images and the GUI images and the textual data are also processed by a media editor 124. The media editor 124 is configured to combine the acquired images, the images of the GUI and the textual data as well as other imaged data such as acoustic data and further video images in order to generate a multimedia video clip coded as a multimedia file according to one or more of the current available coding protocols for video and acoustic files.

Acoustic data may be generated by the ultrasound system such as the audio files representing the hematic flows in the various flow imaging modes such as Doppler, power Doppler, etc. According to a variant shown in FIG. 1, the acoustic data can be generated by a microphone 121 capturing noises or speeches held by one or more of the operators using the ultrasound system. Microphone signals are fed to an audio processor 123 which is configured to code the acoustic signals in audio files. The audio files are fed to the media editor for being associated to one or more of the further images in a synchronized manner with the content of at least one of the said images.

Image data may be captured by a camera 120 reproducing the ultrasound system or part of it, the patient or an anatomic district of a patient and at least one of the operators of the ultrasound system. The image data acquired by the camera is processed by a video processor 122 and also fed to the media editor for being combined in a multimedia representation with the audio files and/or with one or more of the acquired images and/or with the GUI images and/or with the images reproducing textual or alphanumeric coded data.

The media editor 124 may be configured by settings of the user and/or by factory pre-sets to combine the image information and the audio information according to various schemes generating a common multimedia file or the acquired images and/or the GUI images and/or the images reproducing textual or alphanumeric data, the one or more audio files are made available as separate media files which can be downloaded and displayed in parallel in different areas of the display of a client and in a synchronized manner at least for some of the said images and or audio files.

The multimedia files generated by the media editor are fed to a media streaming module 125 which can be accessed through a web server 128 by a client connecting to a communication unit or port 129 of the ultrasound system.

The client is configured to execute a browser which allows access to the multimedia content through the web server 129.

According to a further feature access to the multimedia streaming is regulated by an access control 130 which receives access rights certificates or credentials, such as user ID and password. The access controller 130 compares the certificates sent by the client upon request of the web server 128, with the certificates stored in an access certificate database 131 and if the certificates sent to the access controller 130 corresponds to certificates registered in the said database 131 access to the multimedia streaming module 125 for downloading the multimedia content is allowed.

According to a further feature, the access certificates may also contain parameters indicating which parts of the information coded as acquired images, GUI images, textual and alphanumeric data and audio files may be set free for access by the corresponding client and which parts of the said information is not available for the said client. This parameter is identified and processed by an Information selection controller 132 which is configured to identify the part of the information data to be rendered available for the client that has sent the access credentials and which part has not to be made available. Selection controller 132 may cooperate with the multimedia editor 124 in order to block the transfer of the identified not available data and to allow the access to the available information.

The media editor 124 may also be configured to render part of the visual and or acoustic information not available by covering the display areas where this information is printed on the display screen by a banner and by silencing the audio files or part of them.

According to an embodiment the multimedia files generated by the media editor 124 may be store in a media file memory 133 and the access to the said file by means of the media streaming module 125 can be executed in real-time or at a later time in relation to the time of generation of the visual and/or acoustic information with an off-line streaming process.

The different units and processors 122, 123, 124, 125, 126, 128, 130, 132 may consist all or a part of them in dedicated hardware.

In an alternative embodiment the said units and processors may consist at least for a part of them by a dedicated generic processing unit executing a software program in which the instructions are coded for configuring the generic processing unit in carrying out the functions of the specific processor and/or unit 122, 123, 124, 125, 126, 128, 130, 132.

In a further variant embodiment, at least part of the said units and processors may consist in a software which is executed by the CPU 112 configuring the said CPU and its peripherals for executing the functions of the said at least part of the units and processors 122, 123, 124, 125, 126, 128, 130, 132.

The web server software operates according to the http protocol. Many web server software's may be used among the different currently commercially available web server software's such as for example Apache pf apache Software foundation, nginx of NGINX, Inc., IIS of Microsoft Corporation, Lite Speed Web Server of LiteSpeed Technologies, GWS of GoogleLLC.

Relating to the client many possible web browsers may be executed among which the most popular ones are for example Google Chrome of Google LLC, Mozilla Firefox of Mozilla Corporation, Internet Explorer and Microsoft Edge of Microsoft Corporation.

Examples of media file editors are windows media file editor of Microsoft corporation, MPEG editor of Multimedia Inc. and may other of different softwarehouses.

The multimedia streaming module may be configured according to the Microsoft Multimedia Streaming architecture which is described in https://msdn.microsoft.com/en-us/library/windows/desktop/dd373418(v=vs.85).aspx in the pages linked to this one. The description of this architecture being incorporated by reference herein.

As it will appear more clearly from the following description the any kind of client hardware may be used for connecting to the web server and accessing the multimedia files in the ultrasound system by applying live streaming technology. During the generation of the visual and/or acoustic and/or textual information the same information or only selected part thereof may be downloaded as a multimedia file, in real time in a non limited number of clients and reproduced by the visual and audio reproduction units of the clients, such as a display and loudspeaker.

The multimedia files may be stored in the client for having the possibility of paying them one or more times in an off line process of the client from the server.

Access rights credential hierarchy allow to select the information which is rendered available for specific clients or users.

Being possible to combine different kind of visual information and audio information, it is possible not only to share the images acquired by the ultrasound system and/or combined with the image of the GUI and of possible textual information associated to the acquired images, but it is also possible to record visual and audio information related to tutorial explanation of the system, the way of using and setting it and the way of carrying out examinations such as how to manipulate the probe in relation to the specific anatomic district to be examined.

Figure 2:
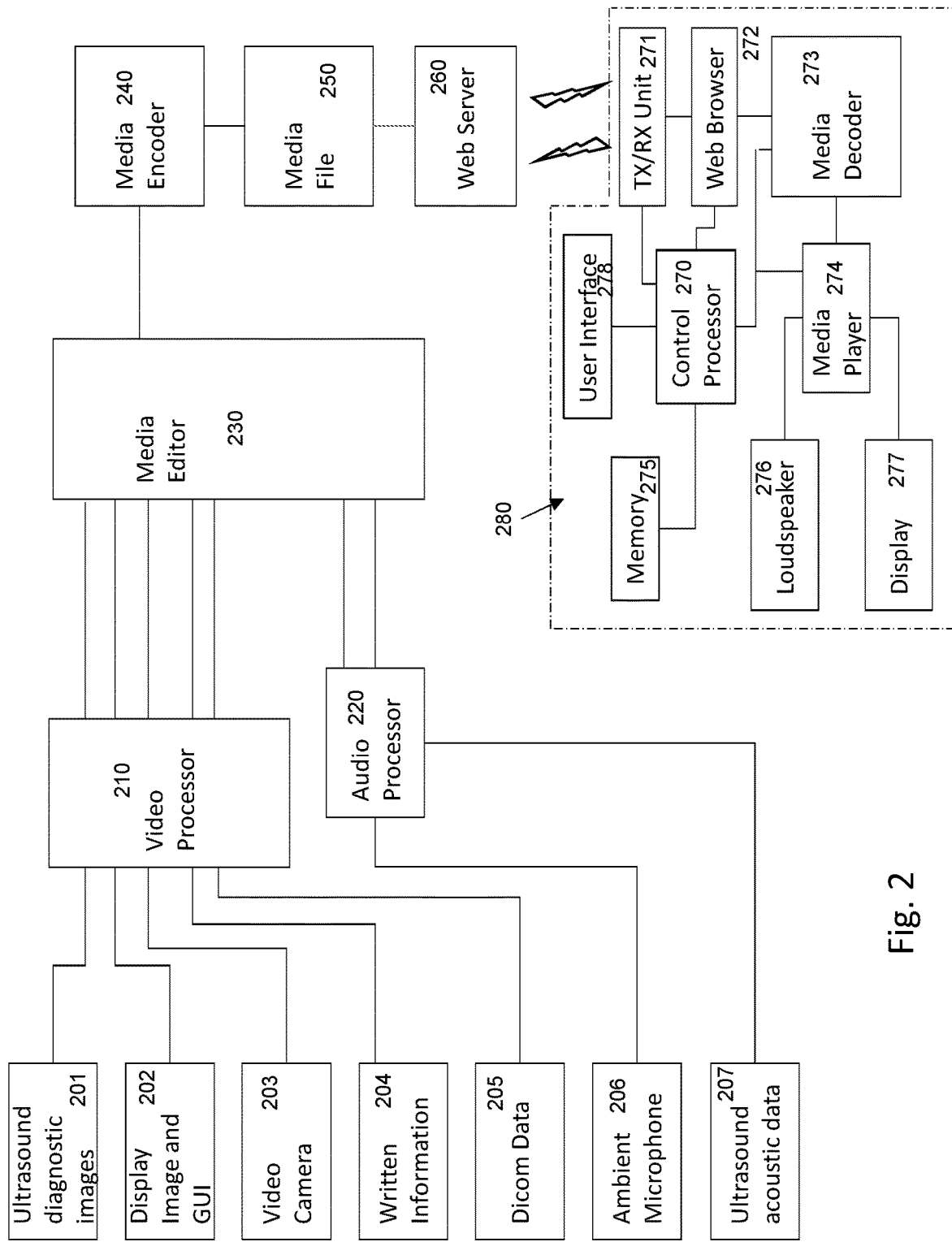
FIG. 2 is a diagram of an embodiment showing the generation units of the multimedia file which can be accessed with a web browser of a client unit connecting to a web server of the ultrasound system.

FIG. 2 shows an exemplary embodiment of a block diagram of the system in which the images generated by different sources and the acoustic information generated by different sources are combined in one or more multimedia files to be accessed, downloaded and played in real time with their generation or at a later time by a streaming technique by one or more clients.

Reference number 201 to 27 shows different sources of images and of acoustic information. The ones shown in FIG. 2 are only an example and further sources may be provided. As an example FIG. 2 shows Ultrasound diagnostic images, Display images of a GUI, Images acquired by a videocamera, textual or alphanumeric data (written data), Dicom Data, audiosignals captured by a microphone, ultrasound audio signals like for example the sounds representing the hematic flows scanned by the ultrasound system in one or more of the so called Doppler modes.

Images are fed to a video processor 210 and acoustic signals are fed to a sound processor 220. These processors generate data files which are fed to a media editor 230 for assembling one or more multimedia files by combining at least part of the visual and/or audio data. The multimedia data are coded in a media encoder 240 and encoded multimedia files 250 are generated which can be downloaded in real-time by accessing them by means of a web browser 272 of a client unit 280. The web browser 272 requesting access to the multimedia file content through the web server 260 by connecting to the ultrasound system communication unit with a TX/RX unit 271. The multimedia data stream is decoded by a media decoder 273 and fed to a media player 274. The media player prints the visual data on a display 277 and the acoustic data is broadcasted by means of a loudspeaker system 276 or similar devices. The multimedia data can be stored in a memory 275 as a multimedia file for allowing to reproduce the multimedia content by the player 2764 at a later time and off-line. A user interface 278 allows the user of the client unit 280 to send access requests to the ultrasound system, to input or modify settings and to carry out selection of stored multimedia file for off-line reproduction or for file management and/or for carrying out standard and usual tasks in relation to maintenance and setting of client devices.

Client devices can be for example workstations, personal computers, tablets, smartphones or similar devices.

Similarly to the embodiment of the ultrasound system the web browser 272, the media decoder 273, the media player 274 may consist all or part of them by hardware or software executed by a processor 270 the said software comprising the instructions to configure the processor 270 and its peripherals to carry out the functions of the said browser 272 and/or media decoder 273 and/or media player 274.

The said software may be in the form of an application installed in the client 280 and executed by the processor 270.

Figure 3:
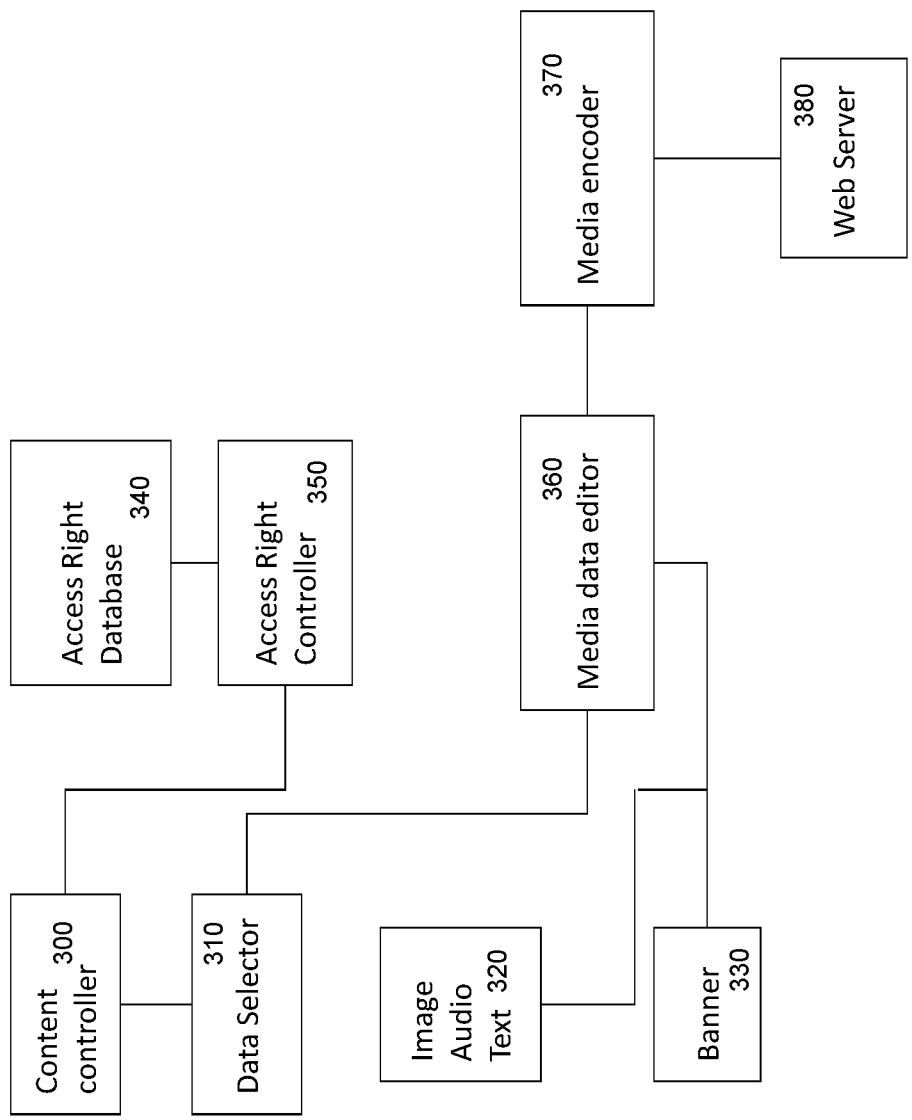
FIG. 3 is a block diagram illustrating an embodiment of the editing of the information in relation to rendering accessible only part of the information as a function of the access rights of the client unit.

In FIG. 3 an exemplary embodiment is shown relating to the functional units for controlling the data which can be rendered available to a certain client or user.

According to this exemplary embodiment a media content controller 300 receives setting data from an access right controller 350 which retrieves this setting data from an access rights database store in a memory 340. The setting information is related to the levels of availability of certain part of the visual, textual and acoustic information which forms the content of a multimedia file to be reproduced by a client. Depending on the credentials associated to the client or to the user of the client some information may be set as not being available for the said user and mat be discarded, from the multimedia file content or simply covered for not being visible for example by a banner provided by a banner graphic generator 330. As a function of the access setting information one or more images or part thereof and/or one or more audio files or part thereof and/or one or more textual information or part thereof as indicated by 320 are selected and processed by the media data editor 360 according to the availability rights defined by the setting data of the access rights. The editor processes the remaining data which can be made available according to one or more of the above examples and renders it available after encoding by the media encoder 370 through the web server 380.

Figure 4:
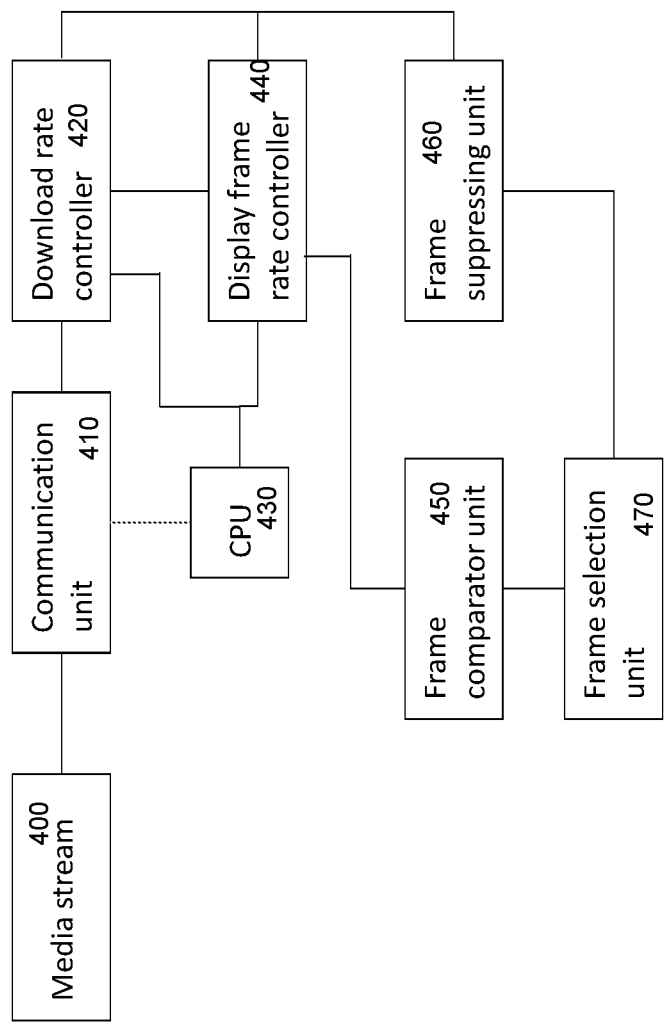
FIG. 4 is a block diagram illustrating an embodiment for controlling the frame rate of the multimedia information reproduced by the client unit.

FIG. 4 shows a further exemplary embodiment of a further feature of the ultrasound system. In order to obviate overloading of the client reproducing in real-time streaming the multimedia content according to the various embodiments disclosed above, the ultrasound system may control the frame rate of the multimedia to be reproduced by the client and eliminates some frames if the frame rate is too high relatively to the available bandwidth and to the processing capability of the client.

According to the shown exemplary embodiment the media stream 400 is transmitted to the client by the communication unit 410. The download speed of the data transmitted is measured by a download rate controller 420. The download rate controller controls a display frame rate controller 440 in which a threshold for a minimum display rate is set. The display frame controller is configured to measure the display frame rate and to compare it to the set threshold. If the measured frame rate is lower than the threshold there is a slowing down of the image sequence and the frame rate controller 440 activates a frame comparator unit 450. The frame comparator unit 450 is configured to carry out a comparation of the visual content of an image frame in respect to a previous image frame and in determining if the two frames are identical. In this event and in the case that the display frame rate is lower than the set threshold a frame selection unit 470 is activated by the Frame comparator unit 450 to select each frame being identical to the previous one and the said selection unit 470 activates a frame suppressing unit 460 for suppressing, discarding or eliminating the said selected frame. Thus image data can be eliminated reducing the data content and allowing to overcome an overloading condition of the client unit. The frame suppressing unit 450 sends messages to the download controller 420 and to the display frame rate controller 440 for repeating the measurements in order to verify if the frame suppression has been successful or a further frame suppressing cycles has to be executed. The process and the controllers are managed by a CPU 430 executing a control program.

Also in this case the controllers and the operative units may consist at least for a part of them of pure hardware or may consist at least for a part of them by a processing unit 430 executing programs in which the instructions are coded for configuring the processing unit to carry out the functions of the said controller and the said units.

Figure 5:
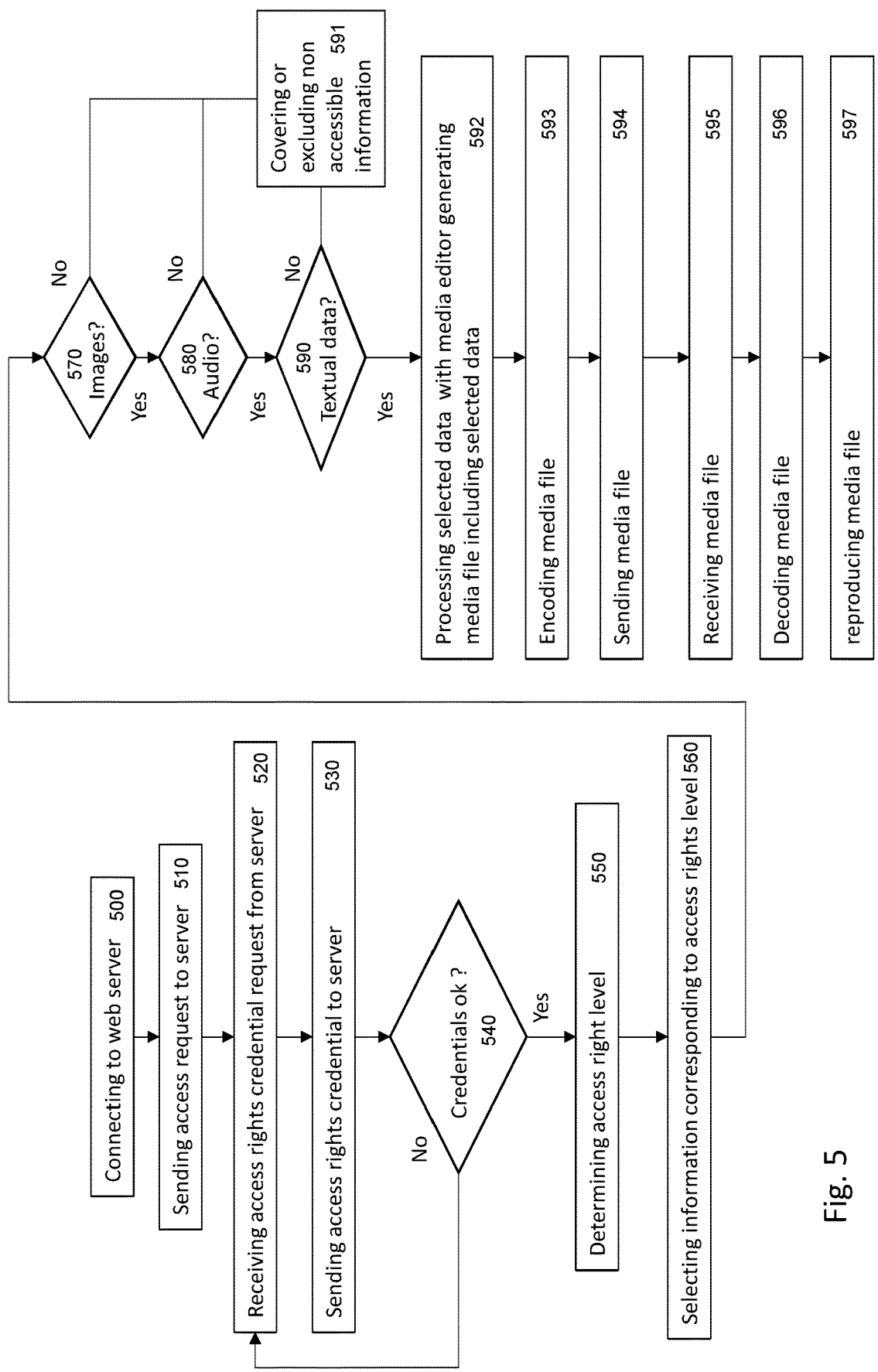
FIG. 5 is a flux diagram illustrating the method of operating the ultrasound scanner according to the embodiments of the preceding figures.

FIG. 5 shows a flux diagram of an exemplary embodiment of the method actuated by one or more of the embodiments of the ultrasound system disclosed.

At step 500 the client device, such as for example a personal computer, a tablet, a smartphone or a notebook or a workstation connects to the web server of the ultrasound system and send at step 510 access requests to the web server for accessing multimedia data by connecting the streaming module. At step 520 the server requests access rights credential to the client and at step 530 these credentials are sent to the server. At step 540 the credentials are verified by the server relating their validity. If the server considers the credentials not valid it requests again the credentials repeating step 520. If the credentials are considered valid the process goes on with step 550 at which the access right level is determined by the ultrasound system for example by a combination of processing units as disclosed in relation to FIG. 1 or FIG. 3. At step 560 the information which corresponds to the access right level is selected by identifying the images, the audio data and the textual data which is to be rendered available to the client and which has not been rendered available to the client as it is indicated by the steps 570, 580 and 590. The information which has not to be rendered available to the client is covered by banners or rendered not available in other ways at step 591.

The information which can be rendered available to the user is processed at step 592 by a media editor for generating a multimedia file including the said data. The multimedia file is encoded at step 593 and sent to the streaming module 594 for being downloaded and played in real time by the client as it is indicated by step 595 and by the following steps of encoding the file at 596 and reproducing the multimedia file 597.

Figure 6:
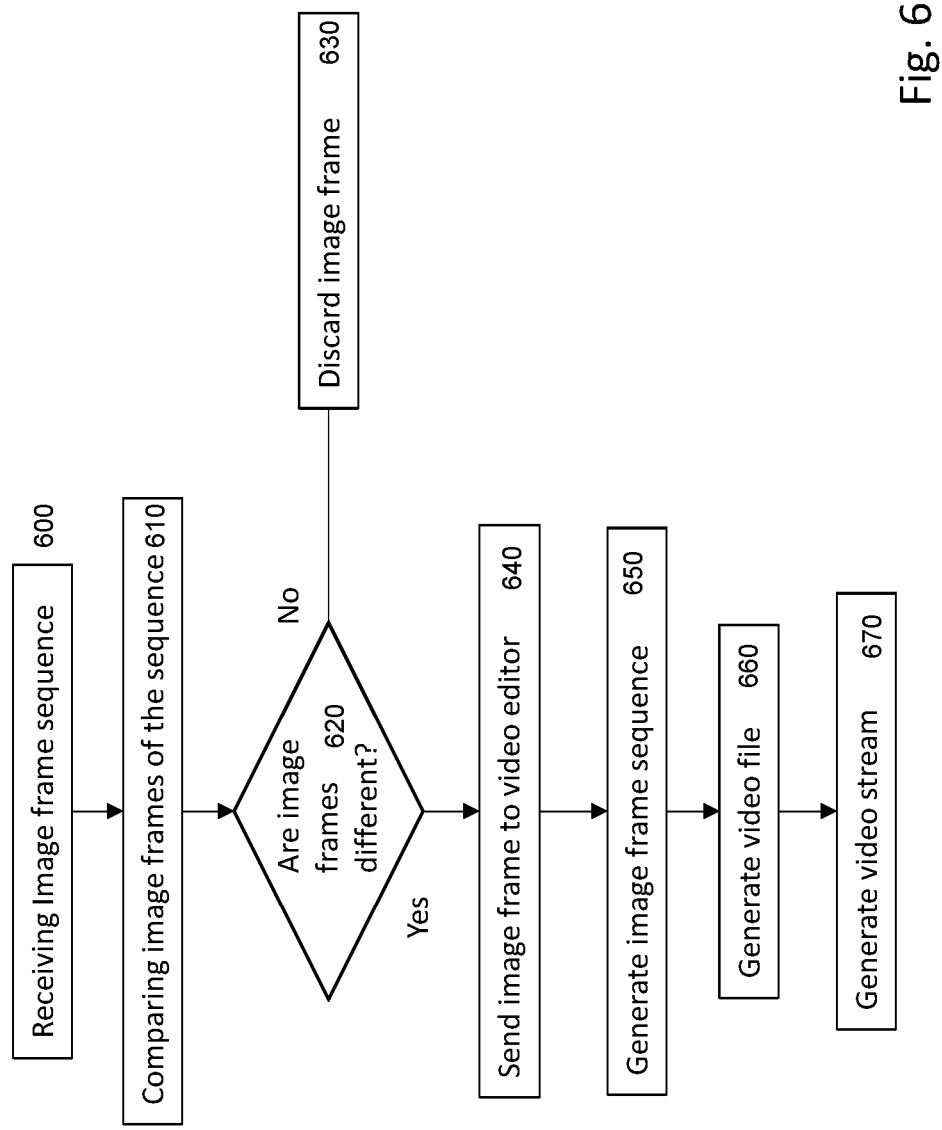
FIG. 6 is a flux diagram illustrating the steps of including in the multimedia stream only frames having different content with respect to the preceding one.

FIG. 6 shows an example of the process for limiting the dimensions of the multimedia file or data by including in the multimedia data stream only the image frames which content is different from previous image frame.

At step 600 a sequence of image frames is received. At step 610 a following frame of the sequence is compared to a preceding one. At the decision step 620, if the result of the comparison is that the frames are identical the following image frame is discarded from the image frame stream used to generate the video file as indicated by the step 630.

The frames having different content are sent in sequence to the video editor at step 640 and an image frame sequence is generated at step 650 the video editor generates a video file of the said frame sequence as indicated at step 660 and the video file is sent to the streaming module as indicated by the step 670.

Figure 7:
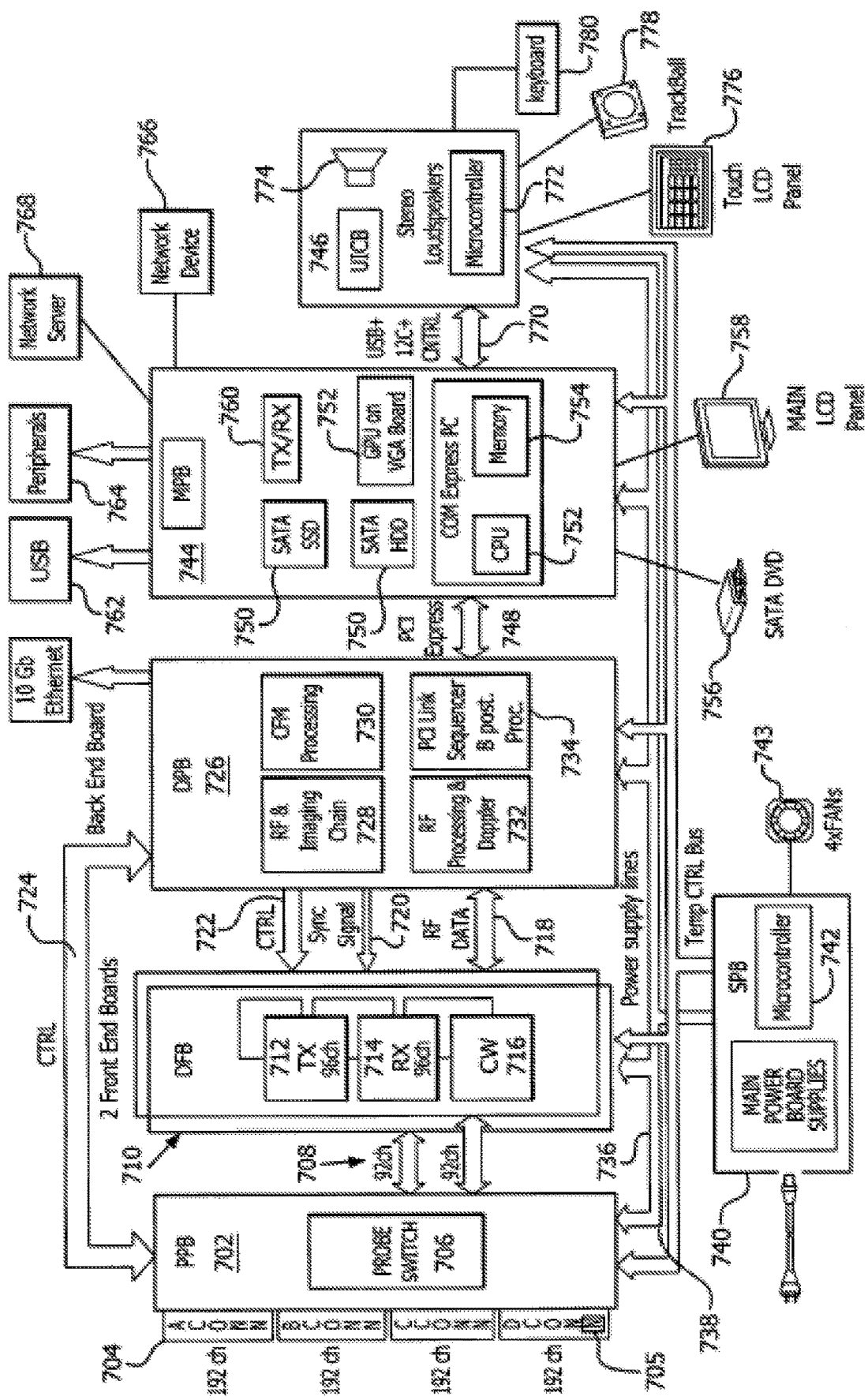
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front-end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front-end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front-end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front-end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front-end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764). The network server may include among others a web server as disclosed in the preceding embodiments providing access to the multimedia files which has been generated by executing programs coding the instructions to carry out the functions relating the processing of the video, audio and textual information and the availability of this information by a streaming technique according to one or more of the preceding claims. The said programs may be executed by one or more of the processors as for example the CPU 752 illustrated in the present figure and also in the following FIG. 9, as for example one or more of the DSP processors 954, 955, 956, 957 and/or 958 and/or 959.

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
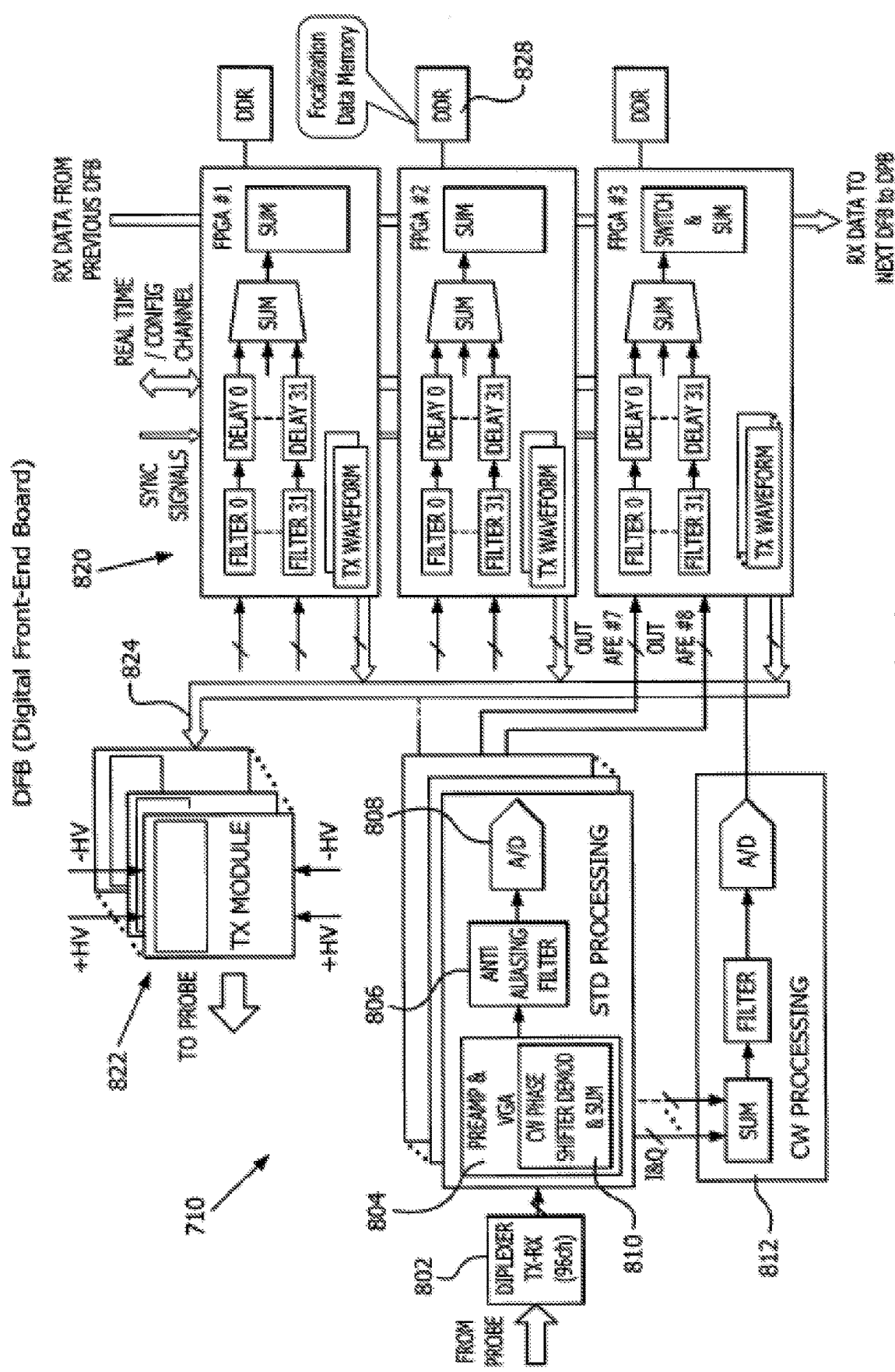
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment the retrospective transmit beam focusing according to the present invention may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
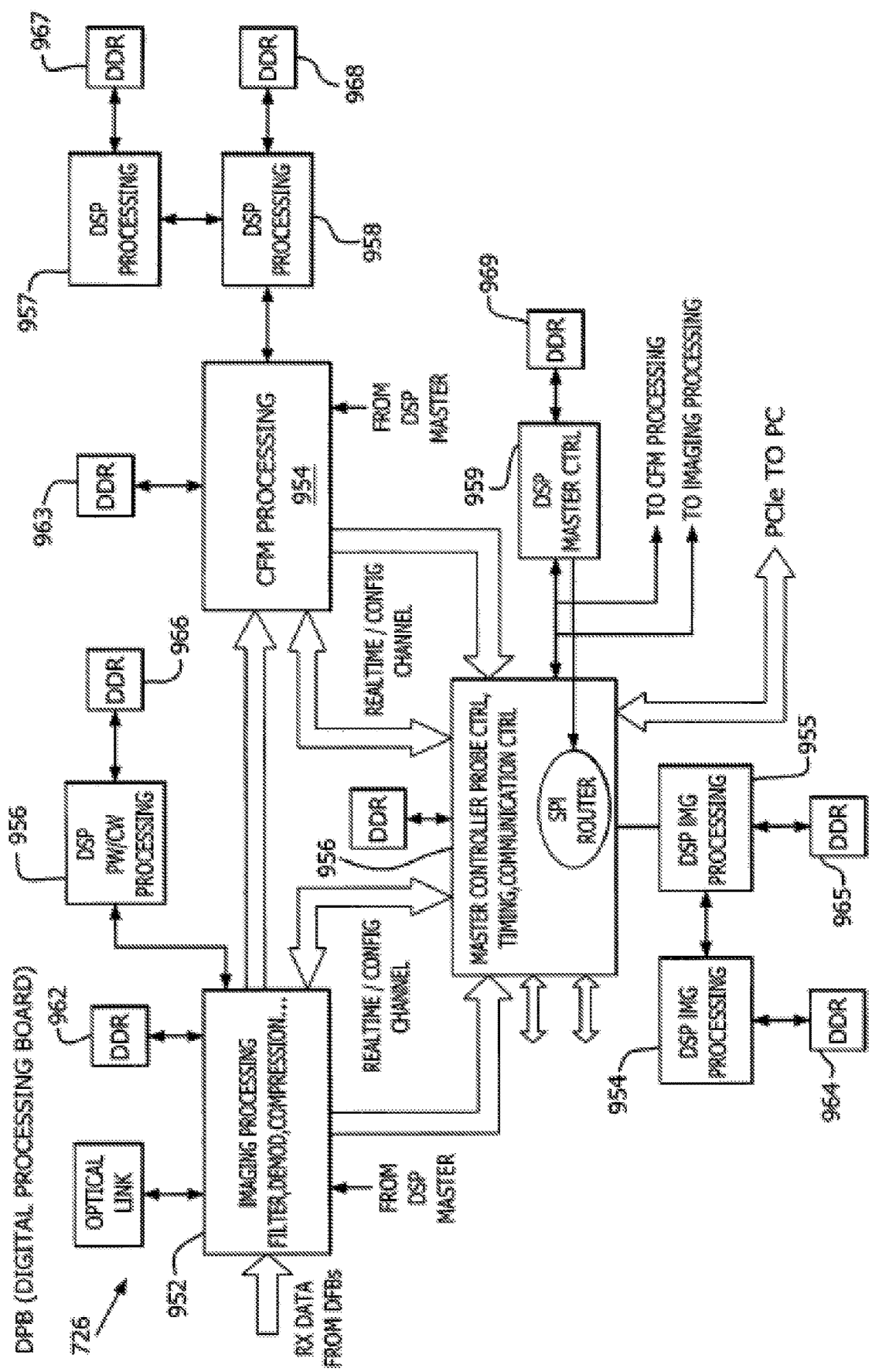
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. An ultrasound system with a multimedia information distribution system comprising:
    a video processor generating a sequence of video frames of at least ultrasound diagnostic images of a sequence of ultrasound diagnostic images;
    a media editor for combining the ultrasound video frames with further audio/video data to generate multimedia data;
    a multimedia encoder encoding the multimedia data in the form of a multimedia file;
    a media streaming module receiving the said multimedia file and generating a real-time stream of the sequence of multimedia data encoded in the said multimedia file;
    a web server allowing access to the real-time stream of the multimedia data upon request by a remote client to access the said multimedia file.

2. An ultrasound system according to claim 1, wherein it is provided in combination with a client unit comprising:
    a processing unit executing a web browser and/or a media file reader executed by the said processor or by a dedicated graphic processor;
    input devices for generating a request of access;
    two-way communication units for sending the request of access to a web server and for connecting to the web server and receiving the multimedia data.

3. An ultrasound system according to claim 1, further comprising a sound processor for generating audio data to be sent to the media editor for combining the audio data with the ultrasound video frames.

4. An ultrasound system according to claim 1, further comprising a text processor for transforming digital alphanumeric information in video data, the said video data being fed to the said media editor which is configured to combine the said textual information video data with the ultrasound video frames.

5. An ultrasound system according to claim 1, further comprising GUI image processor for transforming a GUI image in GUI video data, the said GUI video data being fed to the said media editor which is configured to combine the said GUI video data with the ultrasound video frames.

6. An ultrasound system according to claim 1, further comprising at least a camera oriented to catch a field of view encompassing at least the ultrasound probe, the hand of the operator and the area of use of an object under examination or the entire ultrasound system, the object to be examined and the operator, the video data captured by the said camera being fed to the said media editor which is configured to combine the video data captured by the camera with the ultrasound video frames.

7. An ultrasound system according to claim 1, further comprising at least a microphone for capturing the environmental sounds and especially the voice of at least one operator of the ultrasound system, said audio data captured by the microphone being fed to said media editor which is configured to combine said audio data with the ultrasound video frames.

8. An ultrasound system according to claim 1, comprising an access controller unit configured to receive access rights certificates, validate said access rights certificates by comparing in a comparator unit said access rights certificates with a database of registered access rights certificates stored in a memory and allow access to the web browser of a remote client unit to the multimedia streaming module.

9. An ultrasound system according to claim 8, wherein the access rights certificates are related with selection parameters of the information being available for the owner of the said certificate, the said selection parameter being registered in the database of access rights certificates and the access right controller sending the said selection parameter to a data content controller driving a data selector unit which operates the media data editor to combine only multimedia data related to information available for the corresponding access right certificate.

10. An ultrasound system according to claim 8, comprising a graphic banners generator for generating banners for covering or blending out display area in which non available information for a specific access right certificate are displayed, the said graphic banner generator feeding the banner image to the media data editor for combining the image of the said banner with the ultrasound video frames.

11. An ultrasound system according to claim 1, comprising a controller measuring the frame rate of the displayed frames on the display of the client, said controller being configured to measure the frame rate of the displayed frames and drive a video frame discarding unit from the multimedia data stream to eliminate video frames from said multimedia data stream when the frame rate of the displayed frames falls below a certain threshold, an input interface being also provided for setting said threshold.

12. An ultrasound system according to claim 1, comprising a comparator unit comparing each following video with the preceding one and discarding from the multimedia file to be generated the video frames identical with the preceding ones thus maintaining only the video frames which are different from the preceding ones.

13. A method for distributing visual, acoustic and textual information generated by an ultrasound system in combination with a remote client, the method comprising:
generating video, audio and textual data by an ultrasound scanner;
processing in real time the video, audio and textual data for generating a multimedia file combining at least one or more of the said video, acoustic and textual data;
providing a web server to allow access to the said multimedia file in real time;
providing at least a client connecting the said web server by executing a web browser.

14. A method according to claim 13, further comprising:
providing each client with access certificates;
associating each certificate to a selection parameter determining the kind of information being available for a corresponding certificate;
covering or discarding from the displayed video frames the information which is not available for the corresponding access right certificate.

15. A method according to claim 13, comprising transmitting in the stream of video frames only the video frames having a difference in content from the previous one by:
comparing each video frame with the preceding one;
discarding the identical video frame and freezing the preceding one on the screen;
transmitting for display the following video frame which has differences from the frozen previous one and displaying the said following video frame.

16. A method according to claim 13, comprising:
monitoring the frame rate of the displayed video frames by the client;
comparing the frame rate with a threshold;
suppressing or discarding from the stream some video frames if the frame rate of the displayed frames is lower than said threshold.

\* \* \* \* \*